United States Patent [19]

Ohtani et al.

[11] Patent Number: 5,137,914
[45] Date of Patent: Aug. 11, 1992

[54] SULFONYLAMINO SUBSTITUTED BICYCLO [2.2.1]HEPTANE HYDROXAMIC ACID DERIVATIVES USEFUL AS PHARMACEUTICALS

[75] Inventors: Mitsuaki Ohtani, Nara; Takaharu Matsuura, Hyogo; Kazuhiro Shirahase, Osaka, all of Japan

[73] Assignee: Shionogi & Co., Ltd., Osaka, Japan

[21] Appl. No.: 668,853

[22] Filed: Mar. 15, 1991

[30] Foreign Application Priority Data

Apr. 19, 1990 [JP] Japan .................. 2-103728

[51] Int. Cl.⁵ .................. A61K 31/185; C07C 259/08
[52] U.S. Cl. .................. 514/507; 514/575; 560/312; 562/621; 549/463
[58] Field of Search .................. 549/463; 560/120, 312; 562/502, 621; 514/469, 470, 507, 575

[56] References Cited

U.S. PATENT DOCUMENTS 4,654,357 3/1987 Nakane .................. 549/463
4,960,909 10/1990 Narisada et al. .................. 549/463

FOREIGN PATENT DOCUMENTS 0207684 1/1987 European Pat. Off. .
3346047 6/1984 Fed. Rep. of Germany .

OTHER PUBLICATIONS

Chemical Abstracts, vol. 112, No. 5, Jan. 29, 1990, Abstract No. 112:35549u.

*Primary Examiner*—Bernard Dentz
*Attorney, Agent, or Firm*—Wenderoth, Lind & Ponack

[57] ABSTRACT

Sulfonylamino substituted bicyclyl hydroxamic acid derivatives of the formula:

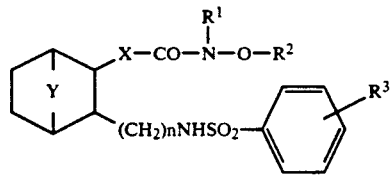

wherein $R^1$ and $R^2$ each is hydrogen or lower alkyl; $R^3$ is hydrogen, lower alkyl, lower alkoxy, hydroxy or halogen; X is alkylene or alkenylene: Y is methylene or oxygen; and n is 0, 1, or 2, or the pharmaceutically acceptable salt thereof. These compounds have an advanced antagonistic activity to thromboxane $A_2$ ($TXA_2$)-receptor and are useful for the treatment of thrombosis, vasoconstriction, or bronchoconstriction, and the like disease which are induced by $TXA_2$.

10 Claims, No Drawings

SULFONYLAMINO SUBSTITUTED BICYCLO [2.2.1]HEPTANE HYDROXAMIC ACID DERIVATIVES USEFUL AS PHARMACEUTICALS

BACKGROUND OF THE INVENTION

1. Field of the Invention

The present invention relates to compounds with an advanced antagonistic activity to thromboxane $A_2$ ($TXA_2$)-receptor, in more detail, to sulfonylamino substituted bicyclyl hydroxamic acid derivatives or the pharmaceutically acceptable salt thereof, which are useful for the treatment of thrombosis, vasoconstriction, or bronchoconstriction, and the like disease which are induced by $TXA_2$.

2. Prior Art

It has been reported that sulfonylamino substitued bicyclyl carboxylic acid derivatives (hereinafter referred to as carboxylic acid derivatives) have potent $TXA_2$-receptor antagonistic activities (JPN Kokai 63-139161, U.S. Pat. No. 4,654,357, EP-A-312,906, and DE 3,720,760, etc.,).

These carboxylic acid derivatives have some drawbacks, namely that they are easily oxidized and metabolized in living tissues. Therefore it has been desired to develop $TXA_2$-receptor antagonists, which are pharmacologically comparable to, but are biologically stabler than the carboxylic acid derivatives.

SUMMARY OF THE INVENTION

The present invention relates to hydroxamic acid derivatives of the following formula (I):

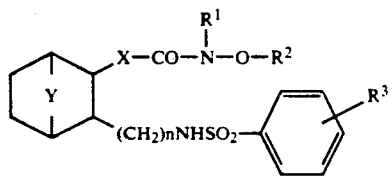

(I)

wherein $R^1$ and $R^2$ each is hydrogen or lower alkyl; $R^3$ is hydrogen, lower alkyl, lower alkoxy, hydroxy or halogen; X is alkylene or alkenylene; Y is methylene or oxygen; and n is 0, 1, or 2. They are very useful for the prevention and the treatment of thrombosis, vasoconstriction, or bronchoconstriction, and the like disease because of their high inhibitory activity against platelet aggregation.

DESCRIPTION OF THE PREFERRED EMBODIMENTS

The present inventors have synthesized a wide variety of compounds and found the hydroxamic acid derivatives (I) as described above satisfy such requirements. This invention is based upon these findings.

In the present specification, "lower alkyl" means $C_1$-$C_6$ alkyl, including, for example, methyl, ethyl, propyl, isopropyl, n-butyl, tert-butyl, and hexyl. Preferred is methyl, ethyl, or propyl.

"Lower alkoxy" means $C_1$-$C_6$ alkyloxy, including, for example, methoxy, ethoxy, propoxy, isopropoxy, n-butoxy, tert-butoxy, and hexyloxy. Preferred is methoxy, ethoxy, or propoxy.

"Halogen" means fluorine, chlorine, bromine, or iodine.

"Alkylene" means $C_4$-$C_7$ alkylene, including, for example, tetramethylene, pentamethylene, hexamethylene, and heptamethylene.

"Alkenylene" means $C_4$-$C_7$ alkenylene, including, for example, 1-butenylene, 2-butenylene, 3-butenylene, 1-pentenylene, 2-pentenylene, 3-pentenylene, 4-pentenylene, 1-hexenylene, 2-hexenylene, 3-hexenylene, 4-hexenylene, 5-hexenylene, 1-heptenylene, 2-heptenylene, 3-heptenylene, 4-heptenylene, 5-heptenylene, and 6-heptenylene. Preferred is 1-pentenylene, 2-pentenylene, 3-pentenylene, 4-pentenylene, 1-hexenylene, 2hexenylene, 3-hexenylene, 4-hexenylene, or 5-hexenylene.

The compounds of the present invention are hydroxamic acid derivatives as explicated by the formula, so such a pharmaceutically acceptable salt as anticipated by a person with ordinary skill in this art is included in the scope of the present invention. Furthermore, the compounds of the present invention have four asymmetric centers as shown in the formula (I) and therefore the scope of this invention extends to all the possible stereoisomers. Among others, it is most preferable to use the present compounds in an optically active form of the following formula:

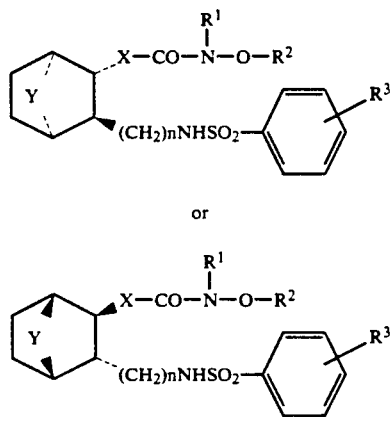

wherein $R^1$, $R^2$, $R^3$, X, Y, and n each is the same as defined before, but it is also acceptable to use them with an optical impurity for the purpose of this invention because of their remarkably high activities.

Furthermore, in the case $R_1$ is hydrogen in the formula (I), the tautomers thereof are also included in the scope of the present invention.

It is thought that the hydroxamic acids moieties at the 2-position of the bicyclic skeleton contribute to an improvement of the biological stability and/or the partial agonistic action.

Therefore, the lower alkyl, lower alkoxy, hydroxy, or halogen substitution on the phenyl ring of the phenylsulfonylamino group, which is another side chain, may be substituted at any position.

The present inventors denote that preferred are those compounds unsubstituted or substituted by methyl, hydroxy, chloro, or bromo at the 4-position of the phenyl in the light of their main effect. Hydroxy may be esterified with acetyl, etc.

Furthermore, it can be expected that conversion of carboxylic acids to hydroxamic acid derivatives improves the biological stability and/or decreases partial agonistic action in thromboxane $A_2$-receptor antagonists.

The acceptable salts of the compounds of the present invention mean salts formed with an alkali metal such as lithium, sodium, or potassium, an alkaline earth metal such as calcium or magnesium; an organic base such as triethylamine, azetidine, 2-phenylimidazole, 1,4-diaminobutane, n-butylcyclohexylamine, dicyclohexylamine, hexamethylenediamine, 3-methyl-3-aminopentane, piperidine, 2,2,6,6-tetramethylpiperidine, 2,2,4-trimethylpiperidine, 2-hydroxypyridine, 4-hydroxypyridine, 2,4,6-trimethylpyridine, tetrahydro-2-methylpyridine, or pyrrolidine. Particularly the salt formed with sodium potassium, or calcium, etc. is preferable.

The compounds (I) of the present invention can be prepared, for example, by condensing amines of the formula (II):

wherein $R_1$ and $R_2$ each is the same as defined before, with the compounds of the formula (III):

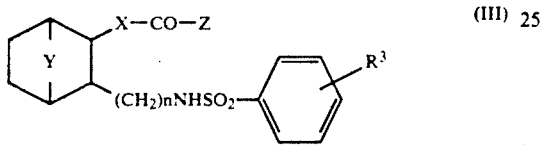

wherein $R^3$, X, Y, and n each is the same as defined before; and Z means an electron withdrawing group.

"Electron withdrawing group" means any group which can activate carbonyl. Those used in a usual acylating reaction may be employed.

The present reaction may be performed according to a conventional manner for synthesizing hydroxamic acids, which is disclosed in ORGANIC CHEMISTRY, Vol. 12 III, 406–432 (Academic.Press).

The starting materials may be prepared according to the disclosure in JPN Kokai 63-139161, JPN Patent Application 1-314028, U.S. Pat. No. 4,654,357, or EP-A-312,906, etc.

The compounds of the present invention can inhibit effects caused by thromboxane $A_2$, so are very useful for the prevention and the treatment of inflammation, hypertension, thrombosis, cerebral apoplexy, cardiac infarction, and cerebral infarction.

Futhermore, known $TXA_2$-receptor antagonists give very preferable biological effects if administered orally so as to give a mild elevation of the blood level of the drug, but show unfavorable side effects if administered in such a one-shot intravenous injection as to rapidly give a high blood level, because of their $TXA_2$-receptor agonistic action (partial agonistic action) after administration, although they are transient.

On the other hand, the compounds of the present invention have substantially no or reduced partial agonistic activities, as explained later. As stated before, it is needless to say that those which have no or substantially no partial agonistic activities are particularly suitable for injection use. Furthermore, if necessary, the compounds of the present invention can be formulated for inhalation, oral, or suppository use, because of their good stability and absorbability.

The compounds of the present invention may be used in conventional formulations for oral use, including solid preparations such as tablets, powder, capsules, and granules, and liquid preparations such as aqueous or oily suspensions, syrups, and elixirs. They can be administered to mammals, including humans. For parenteral use, the compounds of the present invention may be aqueous or oily suspensions for injection. When preparing such formulations, conventional additives may be used, such as fillers, binders, lubricants, aqueous or oily solvents, emulsifiers, and suspending agents, and additionally, preservatives, stabilizers, or the like. It is hard to generally define the dosage of the compounds (I) of the present invention because it depends on the objective therapeutic effect, administration route, age, body weight etc. But usual daily dosage per kg of body weight for an adult is about 0.01 mg to about 50 mg, preferably about 0.05 mg to about 10 mg orally, and about 0.001 mg to about 5 mg, preferably about 0.005 mg to about 1 mg parenterally; in one to five divided doses.

The present invention is further embodied in the following Examples and Experiments, which are not intended to limit the scope of the present invention.

EXAMPLE 1

Preparation of (1R,2S,3S,4S)-(5Z)-7-(3-phenylsulfonyl-aminobicyclo[2.2.1]hept-2-yl)-5-heptenohydroxamic acid (Ia)

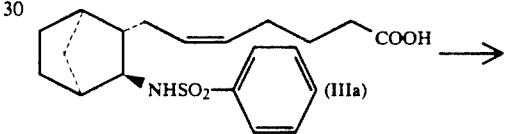

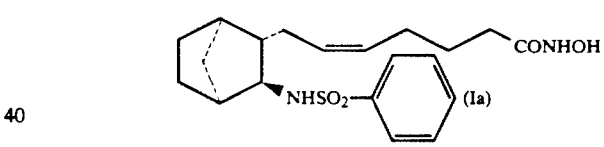

To a solution of (1R,2S,3S,4S)-(5Z)-7-(3-phenylsulfonyl-aminobicyclo[2.2.1]hept-2-yl)-5-heptenoic acid (IIIa) (1.133 g, 3 mM) in dichloromethane (10 ml) is added oxalychloride (915 μl, 3 mM×3.5) under nitrogen atmosphere at room temperature and the mixture is refluxed under mild (50° C.) conditions. After 1 hour, the reaction mixture is evaporated to leave a residue, then benzene is added thereto and the mixture is evaporated again to remove the excess reagent. Hydroxylamine hydrochloride (1.04 g, 3 mM×5) is suspended in THF (10 ml), then a saturated aqueous solution of $NaHCO_3$ (10 ml) is added thereto at room temperature and the mixture is stirred for 5 minutes. To the reaction mixture is added a solution of the acid chloride, prepared before, in THF (6 ml) at room temperature and the mixture is stirred vigorously 1.5 hours. The resulting solution is partitioned between ethyl acetate and 0.5N hydrochloric acid. Then the organic solution is washed with water, dried, and evaporated under reduced pressure to leave a residue, which is recrystallized from dichloromethane/ether to give the objective compound (Ia) (910 mg, yield: 77.1%). colorless pillars mp. 98°-100° C.

IR(Nujol) vmax: 3340, 3246, 1648, 1161, 1093, 1059, 758, 717, 687 cm$^{-1}$.

¹HNMR(CDCl₃) δppm: 0.95-2.30(m, 17H), 3.00-3.13(m, 1H), 5.20-5.43(m, 2H), 5.75(d, J=7 Hz, 1H), 7.45-7.65(m, 3H), 7.80-7.95(m, 2H).

[α]$_D$ +23.7±0.6° (CH₃OH, 1.011%, 25.5° C.).

Elemental/Analysis Calcd. for C₂₀H₂₈N₂O₄S (%): C 61.19, H 7.20, N 7.14, S 8.17, Found. (%): C 61.20, H 7.17, N 7.15, S 8.25.

Sodium Salt of the Compound (Ia)

To a solution of the compound (Ia) (196 mg, 0.5 mM) in methanol (3 ml) is added sodium methoxide (0.163N/methanol) (3.06 ml, 0.5 mM) at 0° C., and the mixture is stirred for a few minutes, then evaporated under reduced pressure to leave a residue, which is dissolved in water, and lyophilized to give quantitatively the sodium salt of the compound (Ia) (207 mg) as a colorless powder.

EXAMPLE 2

Preparation of (1R,2S,3S,4S)-(5Z)-7-[3-(4-hydroxyphenylsulfonylamino)bicyclo[2.2.1]hept-2-yl]-5-heptenohydroxamic acid (Ib)

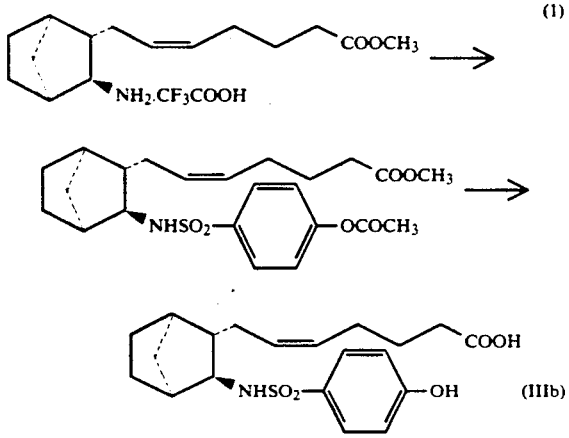

To a solution of methyl (1R,2S,3S,4S)-(5Z)-7-[3-aminobicyclo[2.2.1]hept-2-yl]-5-heptenoate trifluoroacetic acid salt (548 mg, 1.5 mM) in dichloromethane (4 ml) is added a solution of triethylamine (625 μl, 1.5 mM×3) and p-acetoxyphenylsulfonylchloride (360 mg, 1.5 mM) in dichloromethane (2 ml) under nitrogen atmosphere at 0° C., and the mixture is stirred for 20 minutes at the same temperature. The resulting solution is partitioned between ethyl acetate and 2N hydrochloric acid, then the organic solution is washed with water, dried, and evaporated under reduced pressure to leave a residue. Chromatography on silica gel with toluene-ethyl acetate (9:1) as the eluent gave the corresponding sulfonamide (310 mg, yield: 45.9%) as a colorless gum.

To a solution of the compound (300 mg, 0.66 mM) in methanol (3 ml) is added a solution of 1N KOH (2.6 ml, 0.66 mM×4) at room temperature, and the mixture is stirred for 4 hours. The resulting solution is partitioned between toluene and water, then the aqueous solution is acidified with 2N hydrochloric acid and extracted with ethyl acetate. The extract is washed with water, dried, and evaporated under reduced pressure to give 258 mg of the hydroxy compound of the sulfonamide (IIIb) quantitatively as a colorless gum.

¹HNMR(CD₃OD) δppm: 0.96-2.05(m, 14H), 2.12-(brs, 1H), 2.25(t, J=7.4 Hz, 2H), 2.85-2.93(m, 1H), 5.10-5.33 (m, 2H), 6.85-6.95(m, 2H), 7.65-7.75(m, 2H)

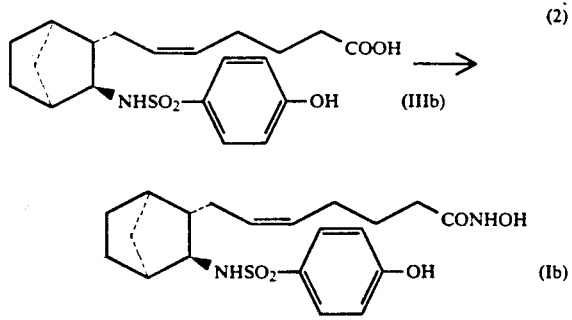

The compound (Ib) of the present invention and its sodium salt are prepared according to the same manner as in Example 1.

Yield: 26.4%, colorless foam.

IR(Nujol) νmax: 3270, 1642, 1604, 1587, 1500, 1148, 1093, 837, 677 cm⁻¹.

¹HNMR(CD₃OD) δppm: 0.97-2.15(m, 17H), 2.85-2.95(m, 1H), 5.10-5.35(m, 2H), 6.85-6.95(m, 2H), 7.65-7.75(m, 2H)

[α]$_D$ +17.5±1.0° (CH₃OH, c 0.561, 22.0° C.)

Elemental Analysis Calcd. for C₂₀H₂₈N₂O₅S.0.2H₂O (%): C 58.28, H 6.96, N 6.80, S 7.78, Found. (%): C 58.47, H 7.02, N 6.81, S 7.35.

EXAMPLE 3

Preparation of (1S, 2S, 3R, 4R)-(5Z)-6-[3-(4-bromophenylsulfonylaminomethyl)-bicyclo[2.2.1]hept-2-yl]-5-hexenohydroxamic acid (Ic)

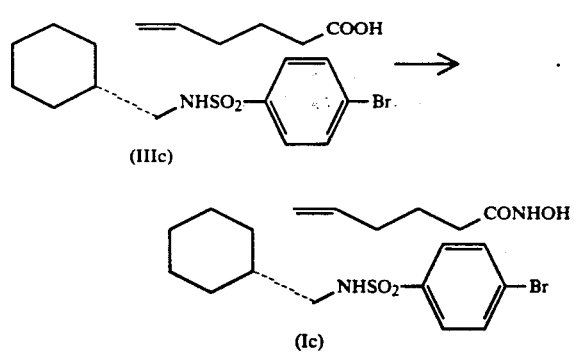

The compound (Ic) of the present invention and its sodium salt are prepared according to the same manner as in Example 1.

Yield: 42.5%, colorless foam.

IR(CHCl₃) νmax: 3360, 1662, 1577, 1471, 1405, 1391, 1331, 1160, 1093, 1069, 1009, 820, 601 cm⁻¹.

¹HNMR(CDCl₃) δppm: 1.10-2.35(m, 16H), 2.75-3.10(m, 2H), 4.95-5.30(m, 2H), 5.27(d, J=9 Hz, 1H), 7.62-7.83(m, 4H).

[α]$_D$ +15.3±0.5° (CH₃OH, c 1.018%, 25.5° C.)

Elemental Analysis Calcd. for C₂₀H₂₇N₂O₄SBr.0.4-H₂O (%): C 50.18, H 5.87, N 5.85, S 6.70 Found. (%):C 50.24, H 5.85, N 6.01, S 6.78.

EXAMPLE 4

Preparation of (1R*, 2R*, 3R*, 4S*)-(5Z)-7-[3-phenylsulfonylamino-7-oxabicyclo[2.2.1]hept-2-yl]-5-heptenohydroxamic acid (Id)

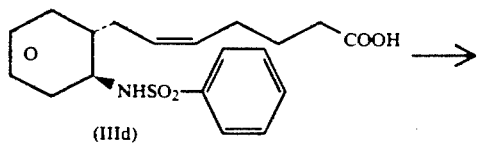

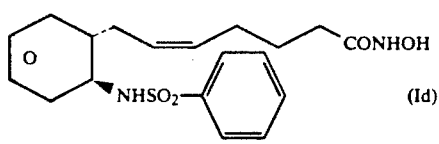

The compound (Id) of the present invention and its sodium salt are prepared according to the same manner as in Example 1.

Yield: 67.4%, colorless foam.

IR(CHCl$_3$) νmax: 3350, 1664, 1447, 1343, 1327, 1160, 1093, 982, 583 cm$^{-1}$.

$^1$HNMR(CDCl$_3$) δppm: 1.20–2.30(m, 13H), 2.86–3.00(m, 1H), 4.02(d, J=4.3 Hz, 1H), 4.42(brs, 1H), 5.10–5.37(m, 2H), 5.63(d, J=9.0 Hz, 1H), 7.47–7.66(m, 3H), 7.84–8.00(m, 2H).

Elemental Analysis Calcd. for C$_{19}$H$_{26}$N$_2$O$_5$S.0.5H$_2$O (%): C 56.55, H 6.76, N 6.94, S 7.94 Found. (%): C 56.66, H 6.65, N 7.11, S 7.74.

EXAMPLE 5

Preparation of (1R, 2S, 3S, 4S)-(5Z)-O-methyl-7-[3-phenylsulfonylaminobicyclo[2.2.1]hept-2-yl]-5-heptenohydroxamic acid (Ie)

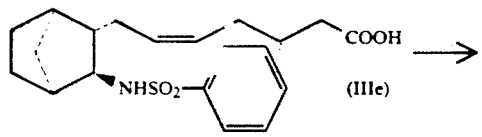

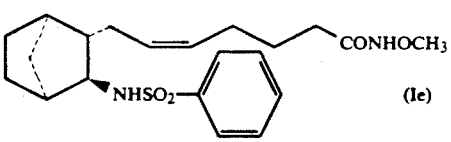

The compound (Ie) of the present invention is prepared according to the same manner as in Example 1.

Yield: 70.7% mp. 78°–80° C.

IR(CHCl$_3$) νmax: 3395, 3280, 3010, 2965, 2885, 1690, 1461, 1450, 1323, 1160, 1095, 590, 555 cm$^{-1}$.

$^1$HNMR(CDCl$_3$) δppm: 0.92–2.26(m, 17H), 2.97–3.10(m, 1H), 3.78(s, 3H), 5.00(brs, 1H), 5.20–5.38(m, 2H), 7.44–7.67(m, 3H), 7.87–7.92(m, 2H), 8.53–8.69(m, 1H)

[α]$_D$: ±17.2±0.6° (CH$_3$OH, 1.032%, 23.0° C.)

Elemental Analysis Calcd. for C$_{21}$H$_{30}$N$_2$O$_4$S (%): C 62.04, H 7.44, N 6.89, S 7.89 Found. (%): C 61.80, H 7.40, N 6.89, S 7.78.

EXAMPLE 6

Preparation of (1R, 2S, 3S, 4S)-(5Z)-N-methyl-7-(3-phenylsulfonylaminobicyclo[2.2.1]hept-2-yl)-5-heptenohydroxamic acid (If)

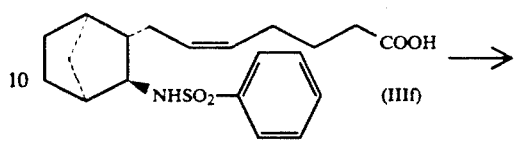

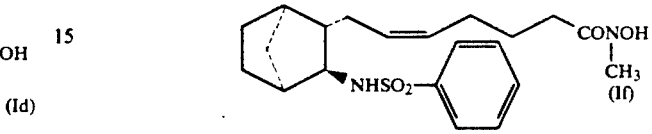

The compound (If) of the present invention is prepared according to the same manner as in Example 1.

Yield: 78.7% mp. 126°–127° C.

IR(CHCl$_3$) νmax: 3300, 3150, 1638, 1148, 1091, 1074, 765, 723, 690 cm$^{-1}$.

$^1$HNMR(CDCl$_3$) δppm: 0.96–2.60(m, 17H), 2.90–3.09(m, 1H), 3.35(s, 3H), 5.22–5.40(m, 2H), 5.72–5.89(brs, 1H), 7.42–7.62(m, 3H), 7.84–7.95(m, 2H)

[α]$_D$: +22.9±0.6° (CH$_3$OH, 1.011%, 25.0° C.)

Elemental Analysis Calcd. for C$_{21}$H$_{30}$N$_2$O$_4$S0.25-H$_2$O(%): C 61.36, H 7.48, N 6.81, S 7.80 Found. (%): C 61.40, H 7.40, N 6.72, S 7.72.

EFFECT OF THE INVENTION

The compounds of the present invention have potent thromboxane A$_2$-receptor antagonistic activity and extremely inhibit platelet aggregation or vasoconstriction, etc. caused by thromboxane A$_2$. This means that the compounds are useful as anti-thrombosis, anti-vasoconstriction agents. In the following Experiment are shown the inhibitory effect of the representative compounds thereof on platelet aggregation in vitro.

EXPERIMENT 1

Antagonistic Activity

Inhibitory Effect on Platelet Aggregation in Rat

[Material and Method]

From the abdominal artery of a male rat (Sprague-Dowley, 7 weeks old) was collected 10 ml of blood with a plastic syringe containing 1.5 ml of ACD (85 mM of sodium citrate, 70 mM of citric acid, 110 mM of glucose) and 20 μg of prostaglandin E$_1$. The blood was placed in a plastic test tube, shaken moderately turning and centrifuged for 10 minutes at 160×g to give platelet rich plasma (PRP). To the prepared PRP was added apyrase (25 μg/ml) and the mixture was layered on 40% bovine serum albumin. The resulting mixture was centrifuged at 1200×g for 25 minutes. The suspension of the prepared platelet pellets in a small amount of a buffer (137 mM of NaCl, 2.7 mM of KCl, 1.0 mM MgCl$_2$, 3.8 mM of NaH$_2$PO$_4$, 3.8 mM of Hepes, 5.6 mM of glucose, 0.035% of bovine serum albumin, pH 7.35) was applied on 10 ml of Sepharose 2B column and eluted with such a buffer to prepare washed platelets.

The platelet aggregation reaction was measured by the aggregometer (NKK HEMA TRACER 1 MODEL PAT-6A.6M, Nikkou Bioscience).

In a measuring curvette was placed 245 μl of the washed platelets which concentration was adjusted to 5×10⁸/μl and set in the aggregometer. The adjusted washed platelets were stirred (1000 rpm) at 37° C. and 3.8 μl of 0.1M CaCl₂ was added thereto. One minute later, 0.5 μl of a solution of a test compound in dimethylsulfoxide was added and 2 minutes later, 1 μl of collagen (Collagen reagent Horm ®, HORMON-CHEMIE München GMBH, final concentration 4 μl/ml) was added as an inducer for platelet aggregation. Platelet aggregation was monitored in terms of the increase and decrease in light transmission.

Concentration of 50% inhibition for platelet aggregation was calculated from the rate of aggregation. (The rate corresponds to light transmission of a sample which was measured at 3 minutes after adding the inducer for platelet aggregation, provided that light transmissions of the washed platelets and the buffer samples are taken as 0% and 100%, respectively.)

The results of the test are shown in Table 1.

TABLE 1

| Compd. No.* | Inhibition for Platelet Aggregation $IC_{50}$ |
|---|---|
| Ia | 12 nM |
| Ib | 10 nM |
| Ic | 20 nM |
| Ie | 60 nM |
| If | 20 nM |
| Rf. Compd. | 2 nM |

*Compounds Ia and Ib were used as their sodium salts.

The reference compound is shown below.

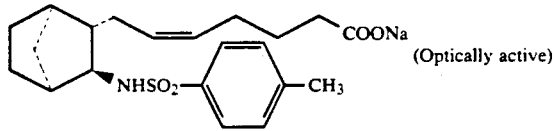

(Optically active)

As clearly shown by the results, the compounds of the present invention have comparable activity for the main effect to known thromboxane A₂-receptor antagonists. Since the reference compound which seems to have the most potent inhibitory activity for platelet aggregation was selected from those disclosed in JPN Kokai 63-139161, the results show the compounds of the present invention have rather lower activity than the reference compound. However it is well known that the compounds of this kind give the same pharmacological effects as those expected by oral administration, if they are intravenously administered at a 1/10 dose of the oral dose. Therefore, considering that the compounds of the present invention are suitable for intravenous administration, it is expected that a smaller dose of them than the reference compound can give pharmacological effects comparable to those expected by oral administration of the reference compound.

Furthermore, partial agonistic activity (activity to induce the shape change in rat platelet) was determined according to the method used for the reaction of platelet aggregation. To the washed platelets was added 0.1M CaCl₂ aqueous solution and 1 minute later, the decrease in light transmission caused by the test compounds was determined to estimate the activity. As a result, the compound (Ia) gave no partial agonistic activity even up to 1000 nM, while the $ED_{50}$ of the reference compound was 1 nM.

The compound (Ia) of the present invention was confirmed to show substantially no partial agonistic activity and longer lasting effects as compared with known carboxylic acid derivatives, by determination of respiration inhibitory activity which is observed when the TXA₂-receptor antagonist is intravenously injected to mice, which is a good index of the partial agonistic activity.

That is, the compound (Ia) of the present invention is very suitable for intravenous injection because of having no partial agonistic activity effect.

What is claimed is:

1. A compound represented by the formula:

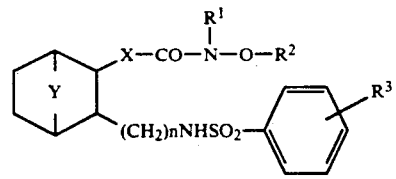

wherein R¹ and R² each is hydrogen or lower alkyl; R³ is hydrogen, lower alkyl, lower alkoxy, hydroxy or halogen; X is alkylene or alkenylene; Y is methylene and n is 0, 1, or 2, or a pharmaceutically acceptable salt thereof.

2. The compound claimed in claim 1, wherein R¹ and R² each is hydrogen.

3. The compound claimed in claim 1, which is a (+)- or (−)-enantiomer.

4. The compound claimed in claim 2, which is a (+)-enantiomer.

5. A pharmaceutical composition comprising a compound claimed in claim 1 as an effective ingredient, in association with a pharmaceutically acceptable, substantially nontoxic carrier or excipient.

6. The pharmaceutical composition claimed in claim 5 for the treatment of thromboxane A₂ mediated disease.

7. The pharmaceutical composition claimed in claim 6, which is in a form suitable for injection.

8. A method for the treatment of thromboxane A₂ mediated disease, which comprises administering an effective amount of a compound claimed in claim 1 to a mammal.

9. The method claimed in claim 8, wherein the administration is carried out through intravenous route.

10. The method claimed in claim 8, wherein the mammal is a human.

* * * * *

UNITED STATES PATENT AND TRADEMARK OFFICE
CERTIFICATE OF CORRECTION

PATENT NO. : 5,137,914

DATED : August 11, 1992

INVENTOR(S) : Mitsuaki OHTANI et al.

It is certified that error appears in the above-identified patent and that said Letters Patent is hereby corrected as shown below:

Column 6, lines 40-53, rewrite as

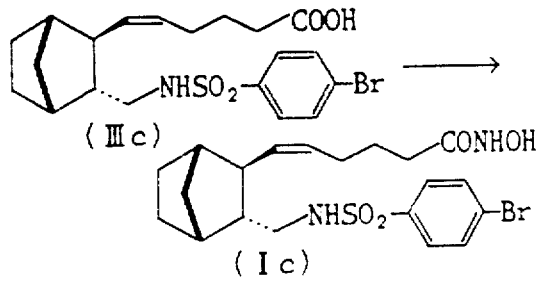

Column 7, lines 7-20, rewrite as

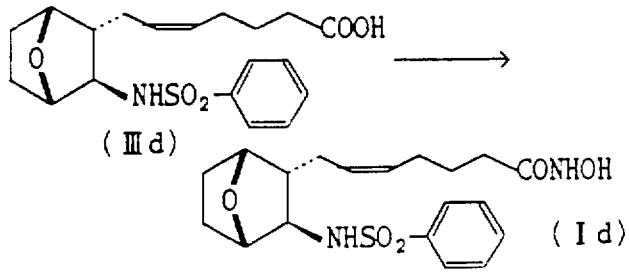

UNITED STATES PATENT AND TRADEMARK OFFICE
CERTIFICATE OF CORRECTION

PATENT NO. : 5,137,914

DATED : August 11, 1992

INVENTOR(S) : Mitsuaki OHTANI et al.

It is certified that error appears in the above-identified patent and that said Letters Patent is hereby corrected as shown below:

Column 7, lines 41-47, rewrite as

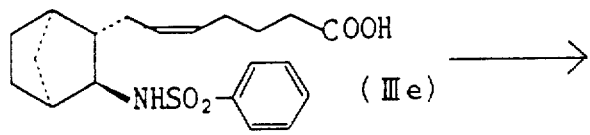

Signed and Sealed this

Twenty-eighth Day of September, 1993

Attest:

BRUCE LEHMAN

Attesting Officer    Commissioner of Patents and Trademarks